United States Patent

Yamakawa et al.

Patent Number: 6,111,405
Date of Patent: Aug. 29, 2000

[54] NONDESTRUCTIVE METHOD OF QUANTITATIVELY EVALUATING DEGREE OF PLASTICITY OF STEEL MATERIAL

[75] Inventors: Hiroshi Yamakawa; Noboru Ishikawa, both of Tokyo; Kazuo Chinone, Chiba; Satoshi Nakayama, Chiba; Akikazu Odawara, Chiba, all of Japan

[73] Assignee: Seiko Instruments Inc., Japan

[21] Appl. No.: 09/118,596

[22] Filed: Jul. 17, 1998

[30] Foreign Application Priority Data

Jul. 18, 1997 [JP] Japan ................. 9-194649

[51] Int. Cl.$^7$ ........................... G01N 27/72
[52] U.S. Cl. ........................ 324/209; 324/227
[58] Field of Search ................. 324/209, 202, 324/227

[56] References Cited

U.S. PATENT DOCUMENTS

| | | | |
|---|---|---|---|
| 5,086,651 | 2/1992 | Westermo et al. | 324/209 X |
| 5,400,656 | 3/1995 | Schiessle et al. | 324/209 X |
| 5,423,223 | 6/1995 | Weinstock | 324/209 X |
| 5,666,051 | 9/1997 | Junker et al. | 324/209 |
| 5,767,671 | 6/1998 | McCoy et al. | 324/209 |

FOREIGN PATENT DOCUMENTS

| | | |
|---|---|---|
| 7744664 | 5/1997 | European Pat. Off. |
| 109412 | 4/1994 | Japan |
| 332641 | 12/1998 | Japan |

*Primary Examiner*—Thomas P. Noland
*Attorney, Agent, or Firm*—Adams & Wilks

[57] ABSTRACT

In a nondestructive method of quantitatively evaluating a degree of plasticity of ferromagnetic materials, a magnetic field of a surface of a ferromagnetic test body is measured using a magnetic sensor, and the surface of the ferromagnetic test body is partitioned into regions corresponding to domains of the ferromagnetic test body. A difference between a maximum value and a minimum value of a magnetic signal corresponding to the magnetic field for each of the domains is calculated as a spatial difference amount. A distribution width of the spatial difference amounts and an amount of residual strain corresponding to an amount of plastic deformation of the ferromagnetic test body is measured. A correlation between the distribution width of the spatial difference amounts and the amount of residual strain is calculated. A degree of plasticity of the ferromagnetic test body in calculated in accordance with the correlation.

9 Claims, 8 Drawing Sheets

NONDESTRUCTIVE METHOD OF QUANTITATIVELY EVALUATING DEGREE OF PLASTICITY OF STEEL MATERIAL

BACKGROUND OF THE INVENTION

The present invention relates to a method of quantitatively evaluating a degree of plasticity of steel material by using a magnetic sensor.

When steel material of a steel skeleton construction or the like used as a structure in a structural entity is applied with overload exceeding the yield point, plastic deformation is caused.

In respect of a structure subjected to a load by a great earthquake or the like, it is important when investigating the continuous use of the structure thereafter, and determining the necessity of reinforcement and the like to determine whether the structural material has been deformed within a range of elastic deformation or plastically deformed by being applied with overload exceeding the yield point.

When plastic deformation is considerable, plasticization of steel material is determined by optical observation or dimensional measurement. However, when the plastic deformation is inconsiderable, the presence or absence of the plastic deformation is difficult to determine since an amount of deformation of the structure is small or is concealed under an interior member of a fire proof cover material covering the steel material.

Therefore, as a conventional method of determining plasticization, there has been only a method of indirectly determining the plasticization by observing a deformed state of a structure, exfoliation of black scale or the like covering the steel material, damage of interior and exterior members or the like, and there has been no effective and pertinent engineering method capable of directly measuring plasticization of a structure.

Meanwhile, as metallurgical methods for determining plasticization of a steel material, there are a method of observing the structure of steel material and observing dislocations or slip lines caused in accordance with plasticization, and a method of oxidizing (etching) the surface of the steel material and optically observing strain-hardened regions.

However, in order to carry out observation of a structure, samples for observing steel material needs to sample therefrom and surface thereof needs to polish and in the case of observing the samples by etching, steel material needs to be etched by a corroding solution after heating it at 250 through 300° C. Accordingly, in either of the methods, observation and measurement can be carried out when small test pieces are used in a laboratory, however, application to an actual structure is difficult.

Further, there has been investigated a method of determining plasticization of a sample by arranging the sample in a detecting coil, applying alternating current thereon and detecting an alternating current magnetizing property as proposed in, for example, Japanese Unexamined Patent Publication No. JP-A-6-109412. However, also in this case, similar to the above-described metallurgical methods, application to an actual structure is invariably difficult.

Further, even when presence or absence of plasticization can be determined by the above-described methods, there has been no method of quantitatively evaluating to what degree steel material is plasticized.

In view of such an actual situation, it is an object of the present invention to provide a nondestructive method of quantitatively evaluating a degree of plasticity of steel material.

SUMMARY OF THE INVENTION

According to one aspect of the present invention, there is provided a nondestructive method of quantitatively evaluating a degree of plasticity of steel material, wherein a magnetic field of a surface of a steel material is measured by a magnetic sensor, the surface of the steel material is partitioned in predetermined sizes and in respect of the magnetic field in each of domains, a difference between a maximum value and a minimum value of a magnetic signal is set as a spatial difference amount;

wherein a distribution width of the spatial difference amount and an amount of residual strain in accordance with an amount of plastic deformation are measured with respect to the steel material which is a test body and a correlation between the distribution width of the spatial difference amount and the amount of residual strain is previously set; and wherein the magnetic field of the surface of the steel material which is a measured body is measured, the spatial difference amount for each of the domains is provided and a corresponding one of the amount of residual strain is calculated based on the correlation.

Plastic deformation of steel material is caused by causing dislocations or slip lines at inside of crystals. Dislocation or slip line is a defect of a lattice and, therefore, nonuniform stress is caused at the surrounding and magnetic anisotropy induced by the stress is caused. The present invention pays attention to the magnetic anisotropy caused by plastic deformation and intends to determine the presence or absence of plastic deformation, degree of plasticity and the like by detecting a change in a magnetic field caused by the magnetic anisotropy.

Figure 12A:
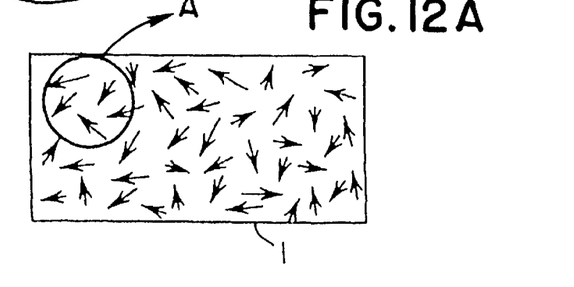
FIG. 12A is a view schematically showing a magnetic domain structure of a steel material.
Figure 12B:
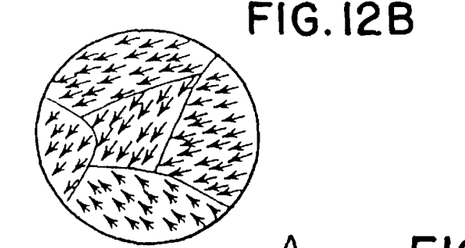
FIG. 12B is a view schematically showing a microscopic magnetic property of the steel material in an elastic region A of FIG 12A.
Figure 13:
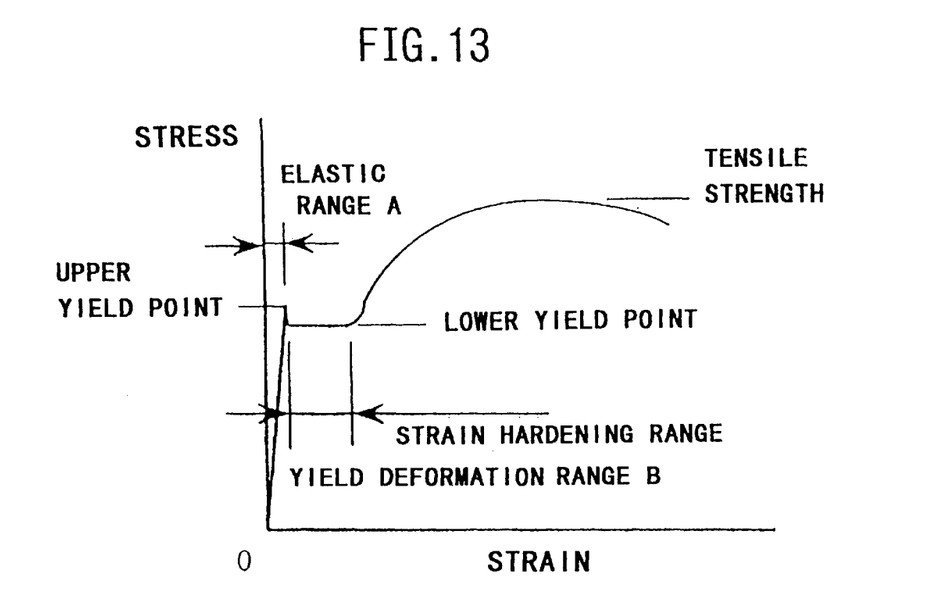
FIG. 13 is a diagram showing a stress-strain curve of steel material.

That is, as shown by FIGS. 12A and 12B a ferromagnetic material such as steel material 1 is provided with a magnetic structure referred to as magnetic domain structure which is partitioned by a number of magnetic domains and a number of magnetic spins respectively directing the same direction are present in each of the magnetic domains. In respect of a stress-strain curve of steel material shown by FIG. 13, directions of magnetization at respective magnetic domains are random in an elastic region A and therefore, the steel material 1 shows isotropic magnetization property as a whole and strain is small.

When a load exceeding the yield point is exerted on the steel material 1, dislocations as well as slip lines which are aggregations of dislocations are caused in the structure. A microscopic stress field is caused at the surrounding of the dislocation or the slip. In the case of a ferromagnetic body such as the steel material 1, the magnetic anisotropy induced by the stress is caused at the vicinity of the stress field.

Figure 14:
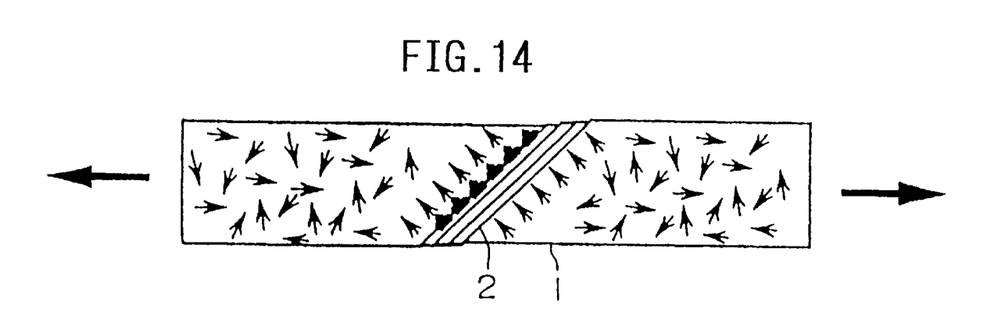
FIG. 14 is a view schematically showing a microscopic magnetic property of steel material where plastic deformation is caused.

Further, when dislocation or slip is increased, nonuniform plastic deformation referred to as a Lüder's band 2 which is an aggregation of these is caused (refer to FIG. 14). A significant magnetic anisotropy is induced at a vicinity of the Lüder's band 2 and as a result, a magnetic field is formed outside of the steel material 1. Hence, by quantitatively measuring the magnetic field, presence or absence of the Lüder's band 2, its position and a degree thereof can be detected and accordingly, plasticization and a degree of plasticity can be determined and evaluated.

However, the steel material 1 is normally provided with a self-occurring magnetic field since it is a ferromagnetic body and a magnetic field inherent to the steel material 1 and a magnetic field caused by plastic deformation are superposed outside of the steel material 1. Accordingly, it is necessary to measure only the magnetic field caused by plastic deformation in order to discriminate and evaluate the plasticization and the degree of plasticity and it is necessary to pick up selectively only the magnetic field caused by plastic deformation by compensating for the magnetic field inherent to the steel material 1.

Hence, according to the present invention, attention is paid to the fact that on the premise where the steel material 1 is not magnetized in a particular direction, spatial distribution of the magnetic field inherent to the steel material 1 is gradual whereas a change in spatial distribution of the magnetic field caused by plastic deformation causing the Lüder's band 2 is large since the Lüder's band 2 is locally caused at inside of the steel material 1, a magnetic sensor of a differential type, that is, a type capable of detecting local change of magnetic field with high accuracy is used and the surface of the steel material 1 is scanned by the magnetic sensor by which the self-occurring magnetic field at a vicinity of the surface of steel material 1 is quantitatively measured as magnetic signals and presence or absence of the Lüder's band 2 is detected and the degree of plasticity is quantitatively evaluated from a planar distribution state thereof.

Further, as the above-described magnetic sensor, there are, for example, a superconducting quantum interference device magnetic flux meter (SQUID magnetic flux meter), a magnetic sensor having a detecting coil of a differential type, a magnetic sensor having offset function and so on.

Figure 15A:
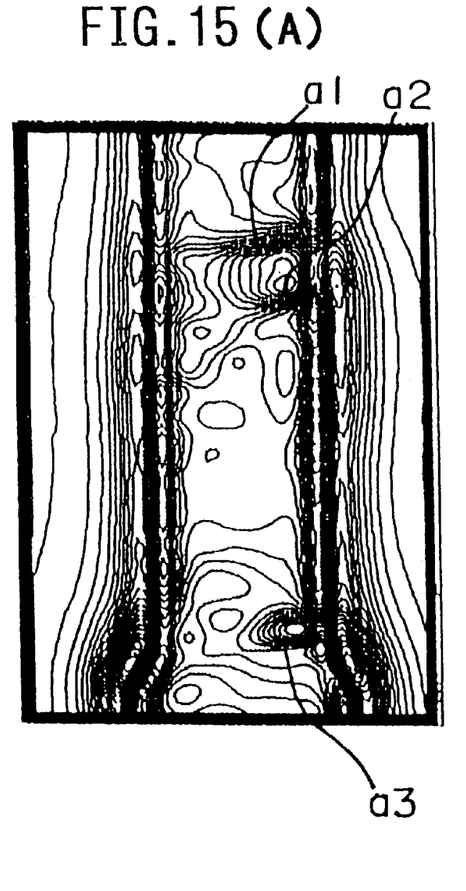
FIG. 15A is an equi-magnetism line diagram of magnetic signal produced by scanning a test body by a magnetic sensor and FIG. 15B is a photograph of Lüder's bands of the test body in correspondence with FIG. 15(A).
Figure 15B:
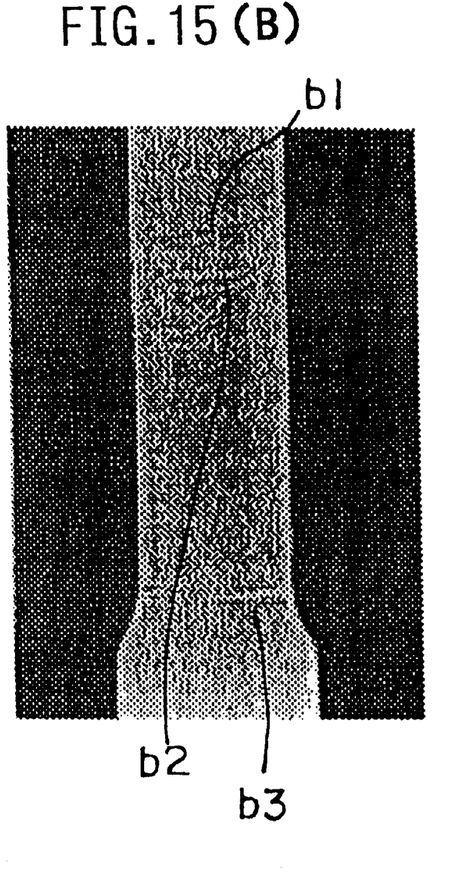

For example, a value of spatial quadratic differential of a magnetic field is measured by scanning the steel material 1 which has been plasticized by using a superconducting quantum interference device magnetic flux meter and an equi-magnetism line diagram is drawn as shown by FIG. 15(A). When a photograph of Lüder's bands of the steel material 1 shown by FIG. 15(B) is compared with the equi-magnetism line diagram shown by FIG. 15(A), portions a1, a2 and a3 of FIG. 15(A) where intervals of equi-magnetism lines are dense, coincide with plastically deformed portions (Lüder's bands) b1, b2 and b3 of FIG. 15(B). Thereby, it can be understood that the portions of the Lüder's bands correspond with the portions a1, a2 and a3 where the intervals of equi-magnetism lines are dense which are provided by magnetic field measurement.

Hence, according to the present invention, in respect of test bodies having respective residual strains, for example, 0.2%, 0.5%, 0.8% and 1.5% residual strain when various magnitudes of tensile loads exceeding the elasticity limit have been applied on a steel member which is the test body, a differential value of a magnetic field is measured by a magnetic sensor, the surface of each of the test bodies is partitioned in predetermined sizes and a difference between a maximum value and a minimum value of the differential value at each of the domains is determined as the spatial difference amount of the test body. Further, a difference between the maximum value and the minimum value of the spatial difference amounts of the test body in accordance with respective amounts of residual strain is calculated as a distribution width.

Figure 11:
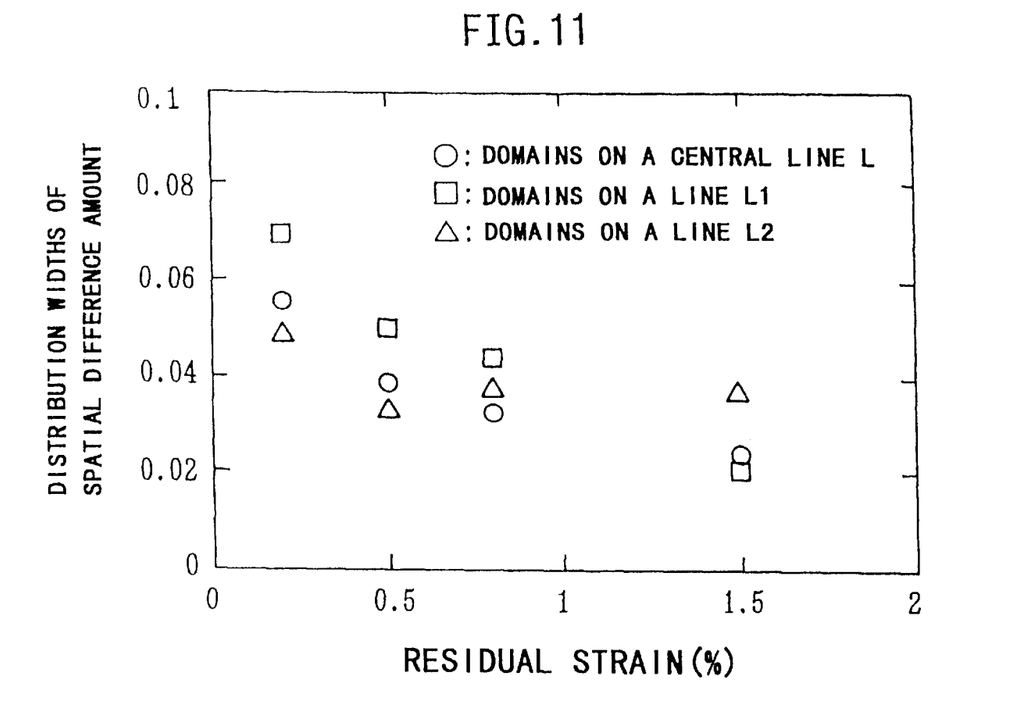
FIG. 11 is a diagram showing relationships between distribution widths of spatial difference amounts and residual strain at respective domains on a central line and two lines on both sides thereof of steel material.

Next, the distribution width of the spatial differential amounts is designated by notation R, the amount of residual strain is designated by notation $\epsilon$ and a correlation between the both is set as shown by FIG. 11. When the correlation is recurred by an exponential function from FIG. 11, it can be represented by the following equation (1).

$$\epsilon = 8.9 \times e^{-67R} \text{ (where } e \approx 2.71828) \quad (1)$$

Next, in respect of steel material which is a measured body, the spatial difference amount is calculated by measuring a differential value of a magnetic field as a magnetic signal by a magnetic sensor and from a distribution width of the spatial difference amounts, an amount of residual strain in correspondence with the distribution width is calculated by using Equation (1) showing the correlation between the distribution width R and the amount of residual strain $\epsilon$. A macroscopic evaluation can be performed with the amount of residual strain as a degree of plasticity.

Further, presence or absence and location of plasticization can be determined by an equi-magnetism line diagram produced from the differential value of the measured magnetic field.

In this way, location of plasticization of steel material can be determined and the degree of plasticity at the location can be quantitatively evaluated as an amount of residual strain.

DETAILED DESCRIPTION OF THE PREFERRED EMBODIMENTS

An explanation will be given of embodiments according to the present invention with reference to FIG. 1 through FIG. 11 as follows.

Figure 1A:
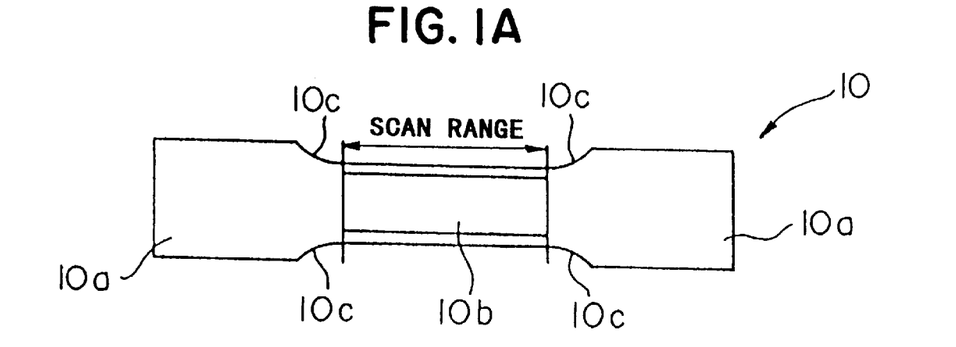
FIGS. 1A and 1B illustrate a plane view, and a side view of steel material which is a test body in a method according to an embodiment of the present invention.
Figure 1B:
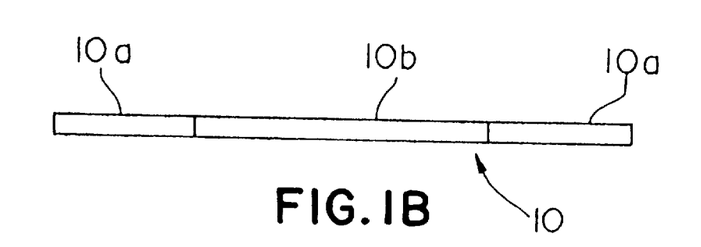
Figure 2:
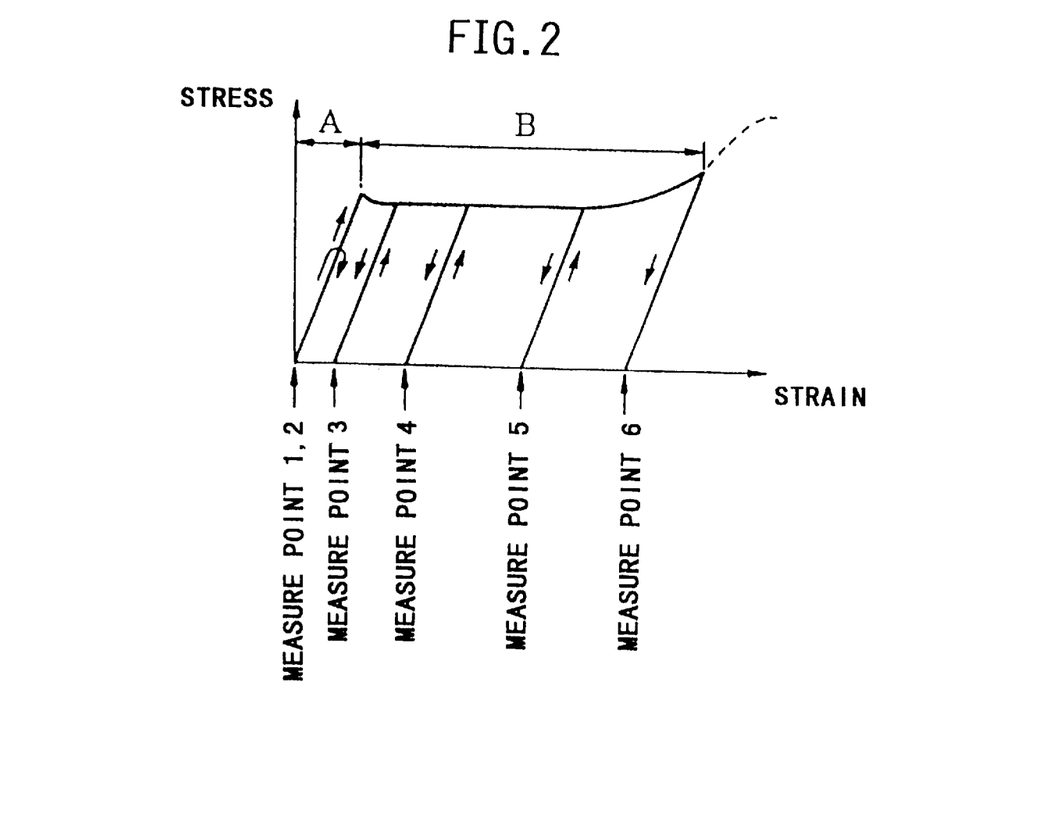
FIG. 2 is a diagram showing magnetism measuring points in a stress-strain curve in respect of deformation behavior of steel material.
Figure 3:
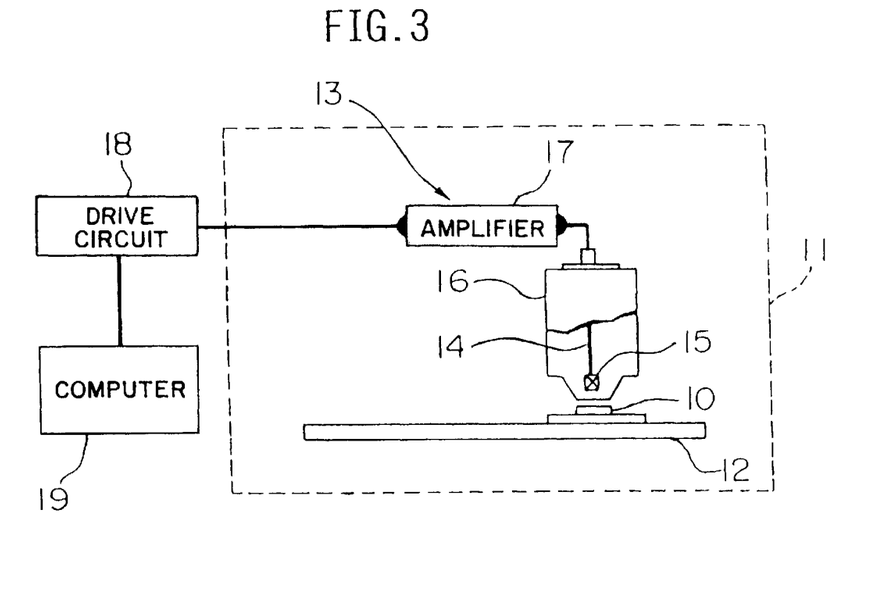
FIG. 3 is a view showing a test body mounted on a moving base in a shield room and being subjected to magnetic field measurement using a magnetic flux meter.
Figure 4:
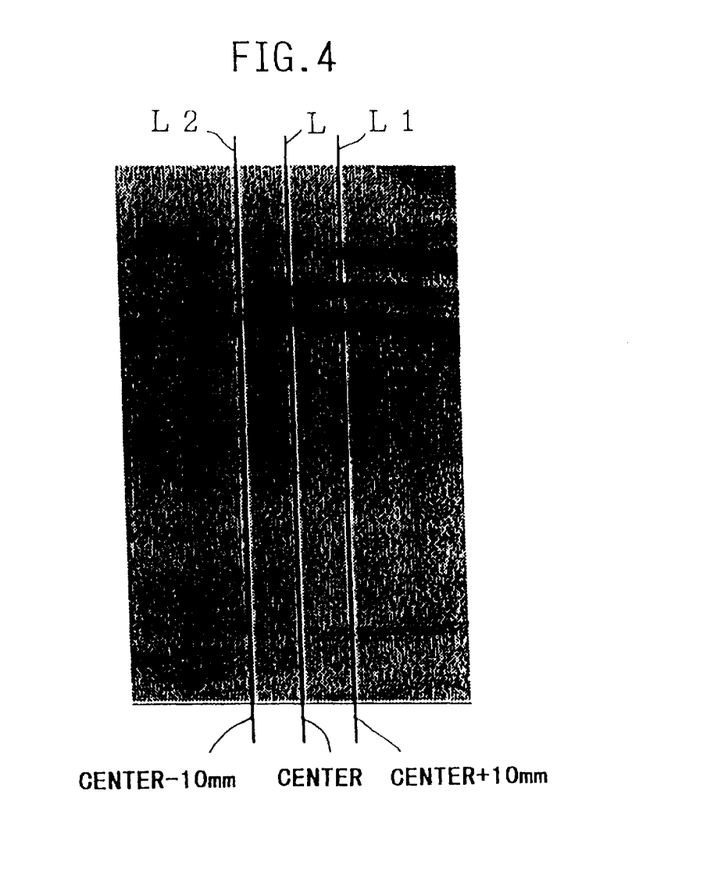
FIG. 4 is a plane distribution diagram showing a change in a spatial difference amount of a test body measured by FIG. 3 by a degree of darkness.
Figure 5:
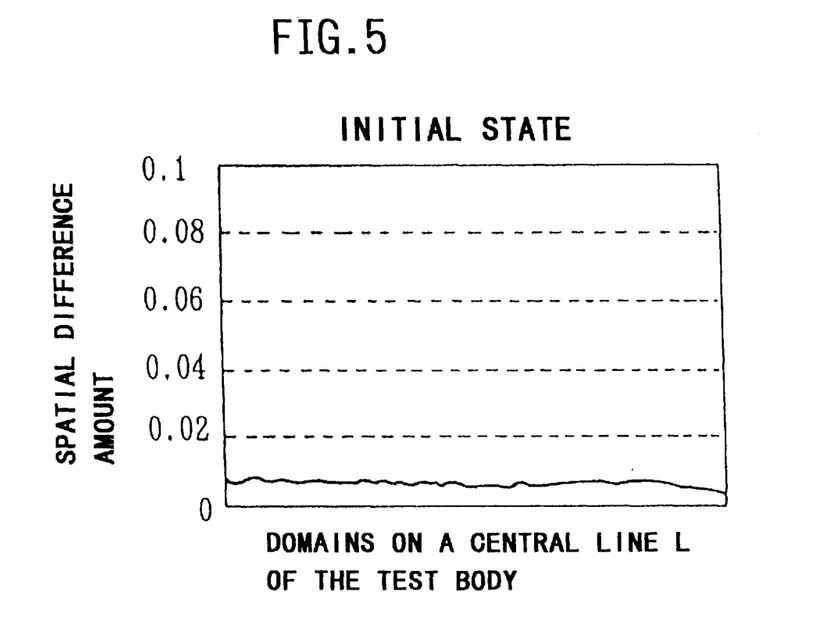
FIG. 5 is a diagram showing a distribution of spatial difference amounts of respective domains on a central line in respect of a test body under an unloaded initial state.
Figure 6:
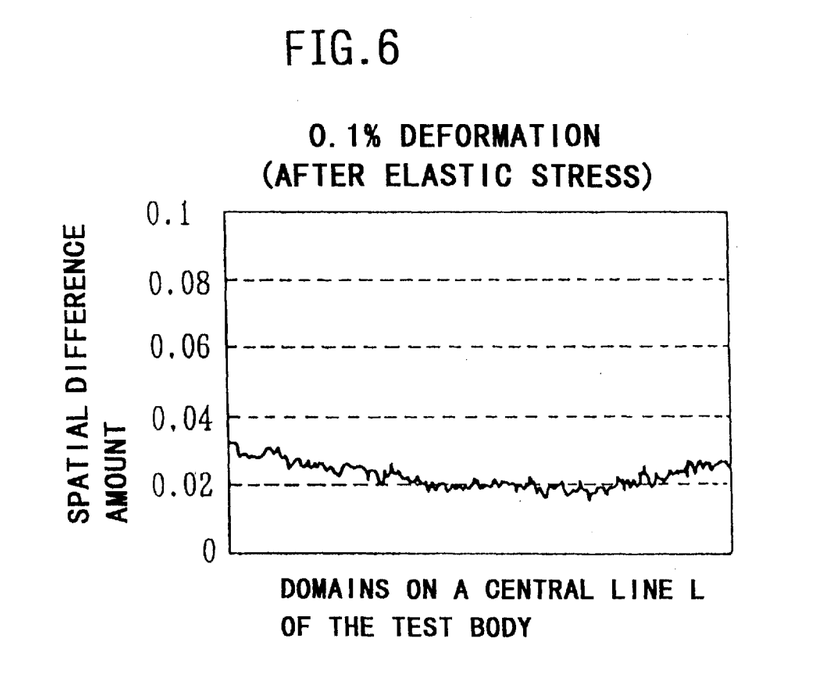
FIG. 6 is a diagram showing a distribution of spatial difference amounts of respective domains on the central line in respect of a test body after having being applied with elastic force with 0.1% deformation (elastic deformation).
Figure 7:
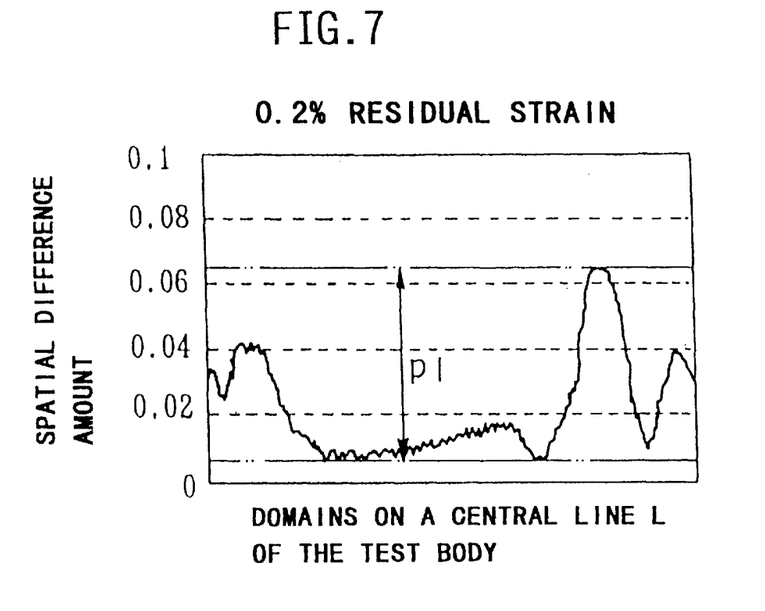
FIG. 7 is a diagram showing a distribution of spatial difference amounts of respective domains on the central line in respect of a test body with 0.2% residual strain.
Figure 8:
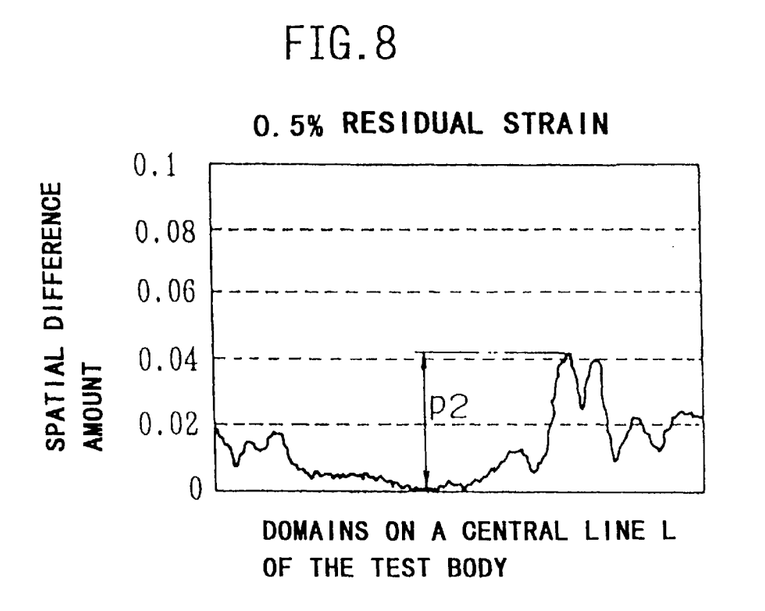
FIG. 8 is a diagram showing a distribution of spatial difference amounts of respective domains on the central line in respect of a test body with 0.5% residual strain.
Figure 9:
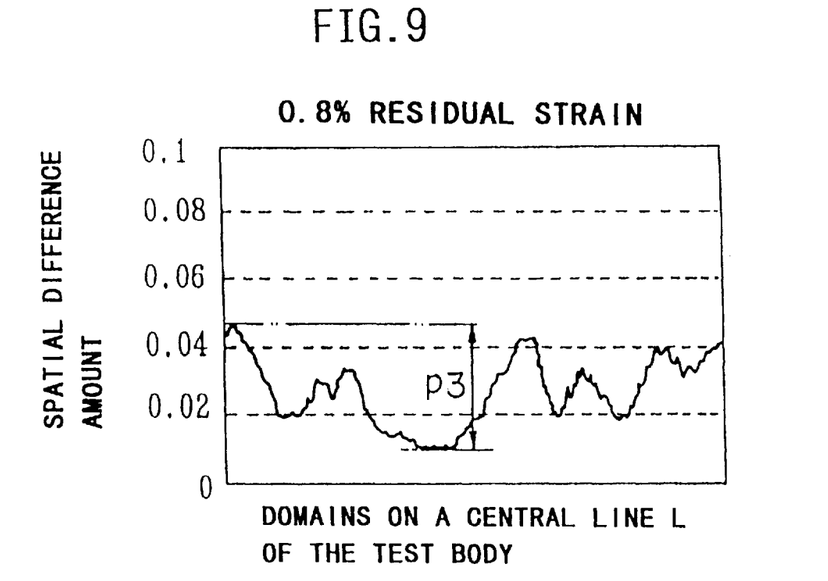
FIG. 9 is a diagram showing a distribution of spatial difference amounts of respective domains on the central line in respect of a test body with 0.8% residual strain.
Figure 10:
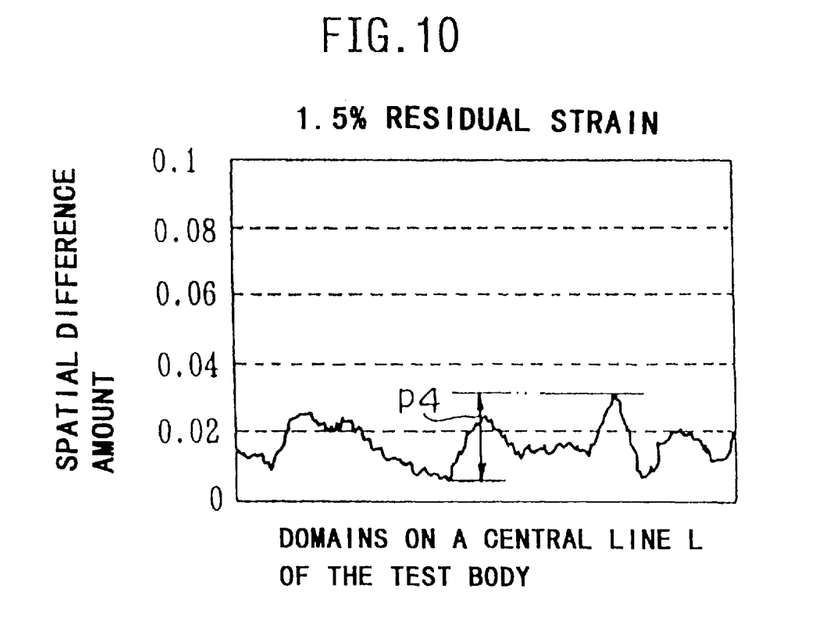
FIG. 10 is a diagram showing a distribution of spatial difference amounts of respective domains on the central line in respect of a test body with 1.5% residual strain.

FIGS. 1A and 1B illustrate a plane view, and a side view of steel material which is a test body in respect of a method according to an embodiment, FIG. 2 is a diagram showing a stress-strain curve and respective measuring points with regard to deformation behavior of steel material, FIG. 3 is a view showing a state of measuring a magnetic field of a test body by using a magnetic sensor, FIG. 4 is a plane distribution diagram showing a magnetically varying value (spatial difference amount) of the test body measured in reference to FIG. 3 by a degree of darkness of color, FIG. 5 is a diagram showing a distribution of the spatial difference amount at domains on a central line of the test body in respect of the test body in an unloaded initial state, FIG. 6 is a diagram showing a distribution of the spatial difference amount similarly in respect of the test body after having being applied with elastic force with 0.1% deformation (elastic deformation), FIG. 7 is a diagram showing a distribution of the spatial difference amount similarly in respect of the test body with 0.2% residual strain, FIG. 8 is a diagram showing a distribution of the spatial difference amount similarly in respect of the test body with 0.5% residual strain, FIG. 9 is a diagram showing a distribution of the spatial difference amount similarly in respect of the test body with 0.8% residual strain, FIG. 10 is a diagram showing a distribution of the spatial difference amount similarly in respect of the test body with 1.5% residual strain and FIG. 11 is a diagram showing a relationship between a distribution width and a residual strain of the spatial difference amount in respect of each of the domains on the central line and two lines on both sides thereof of steel material.

FIGS. 1A and 1B show an example of a steel material 10 in a plate shape used as a test body (hereinafter, referred to as test body). The material is, for example, SM490M, and the test body 10 is thermally degaussed by heating it in an hydrogen atmosphere after having been worked into a predetermined shape. The test body 10 is formed by connecting wide width portions 10a on both sides and a narrow width portion 10b disposed between the wide width portions 10a as a magnetically varying value analyzing portion having a narrow width. The test body 10 is provided with, for example, a total length of 100 mm, a plate thickness of 5 mm, a width dimension of 60 mm for the wide width portion 10a and 40 mm for the narrow width portion 10b, a length dimension of 70 mm for the respective wide width portions 10a and 100 mm for the narrow width portion 10b, and a length of curved portions 10c connecting the wide width portions 10a and the narrow width portion 10b of about 20 mm, respectively.

Tensile load is applied on the test body 10 by pulling both end portions thereof by using, for example, a 490 kM universal tester (not illustrated) as a load tester. A pair of Π type displacement meters are attached (not illustrated) on the both ends of the test body 10 and applied load exerted by the 490 kM universal tester is controlled. Further, an amount of residual strain after removing the tensile load is measured by the Π type displacement meters.

A relationship between stress and residual strain by the tensile load (tensile force) applied on the test body 10 by the tester is shown by a combination of history of the tensile force and magnetism measuring points (measuring points 1 through 6 in FIG. 2) as illustrated by FIG. 2.

Tensile force in elastic deformation and after work hardening is controlled by the load. Magnetism measurement (measuring point 1 through 6 in FIG. 2) using a magnetic flux meter 13 is carried out after applying tensile load on the test body 10 and the load is removed. A region of the measuring points 1 and 2 is an elastic region A with a loading condition of "unloaded initial state" or "under elastic force with 0.1% deformation" and when the tensile load is removed, the test body returns to the original state by elastic deformation and when the tensile load exceeds the upper yield point, residual strain remains.

In respect of regions of measuring points 3, 4, 5 and 6, load is applied such that "0.2% residual strain", "0.5% residual strain", "0.8% residual strain" and "1.5% residual strain (work hardening region)" are resulted which are respectively loading conditions exceeding the lower yield point and force is applied such that the respective amounts of residual strain are resulted. When stress exceeds a yield deformation region B and reaches a strain hardening region, the test body 10 is ruptured.

The test bodies 10 after having being applied with load under respective loading conditions mentioned above, are mounted on a moving base 12 in a shield room 11 as shown by FIG. 3 at respective stages and are subjected to magnetic field measurement. By carrying out magnetism measurement inside of the shield room 11, the test bodies 10 are prevented from being influenced by outside magnetism.

For measuring a magnetic field, for example, a superconducting quantum interference device (SQUID) magnetic flux meter 13 (hereinafter, may be referred to simply as magnetic flux meter) having a quadratic differential detecting coil of a concentric circle type, is used. The magnetic flux meter 13 is arranged with a dewar 16 having a probe 14 and a quadratic differential detecting coil 15 of a concentric circle type at inside thereof opposed to the test body 10 and the dewar 16 is connected to a drive circuit 18 outside of the shield room 11 via a head amplifier 17 and provided measurement data is inputted to a computer 19 and stored there.

The detecting coil 15 is arranged separately from the test body 10 and in parallel with the surface of the test body 10 and detects a quadratic differential value of a magnetic flux density in respect of a direction vertical to the surface of the test body 10 as measurement data.

The surface of the test body 10, after having been applied with and removed of the respective loads mentioned above, is relatively scanned nondestructively by the magnetic flux meter 13 having the quadratic differential detecting coil 15 of a concentric circle type as shown by FIG. 3 and a magnetic field caused by magnetic anisotropy based on the plastic deformation is measured. The detecting coil 15 of the magnetic flux meter 13 is scanned in a noncontact state in respect of the surface of the test body 10 and detects the quadratic differential value of the magnetic flux density in the vertical direction as measurement data (magnetic signal). The measurement data is sampled planely in X-Y directions at a pitch of 1 mm in respect of a range of maximum 100 mm×70 mm which is the narrow width portion 10b of the test body 10 as a magnetically varying value analyzing portion.

Scanned points are set in accordance with a sampling frequency on respective scanning lines from the obtained measurement data of magnetic signal, magnetic field intensities at the respective scanned points are converted into digital values via an A/D converter and an equi- magnetism line diagram as shown by FIG. 15(A) is formed by connecting points having equal magnetic field intensity among the respective scanned points. According to the obtained equi-magnetism line diagram, a dense region having small intervals of equi-magnetism lines and a position of a plastically deformed portion (Lüder's band 2) of the test body 10 as shown by FIG. 15(B) substantially correspond to each other.

Further, a plane distribution of measurement data of the magnetic signal on the surface of the test body 10 is partitioned with a certain size (for example, 5 mm×5 mm square) as a unit and a difference between a maximum value and a minimum value of the magnetic signal in each of the domains is calculated, and the difference is determined as a spatial difference amount (magnetically varying value) as a representative value in the domain. Then, the spatial difference amount is provided with a large value at the plastically deformed portion of the test body 10 and a small value at a portion thereof which is not plastically deformed and, therefore, the domains can be differentiated from each other.

FIG. 4 is a plane distribution diagram showing a value of the spatial difference amount at each of the domains by a degree of darkness in respect of the narrow width portion 10*b* (magnetically varying value analyzing portion) of the test body 10. The darker the color of a region, the more plastically deformed is the region with a larger value of the spatial difference amount, which corresponds to a position of causing the Lüder's band 2.

Next, tensile forces as loading conditions at the respective measuring points 1 through 6 are respectively applied, thereafter, as shown by FIG. 4, the spatial difference amounts at respective domains disposed on a central line L of the narrow width portion 10*b* of the test body 10 in the longitudinal direction are respectively sampled. Further, the spatial difference amounts at the respective points on the central line L are respectively shown by graphs in accordance with the respective loading conditions of the measuring points 1 through 6 as shown by FIG. 5 through FIG. 10.

That is, the spatial difference amounts at the respective domains in an unloaded initial state shown by FIG. 5, remain almost unvaried with 0.1% elastic deformation (after applying elastic force) as shown by FIG. 6, a variation in the spatial difference amounts of the respective domains is only about 0.01 and the variations are small in any of them.

When load exceeding the elastic limit is applied, in the case of residual strain of 0.2%, as shown by FIG. 7, according to the spatial difference amounts, a value less than 0.01% constitutes a minimum value, a value slightly exceeding 0.06 constitutes a maximum value and a difference between the minimum value and the maximum value constitutes a distribution width p1 of the spatial difference amounts. Further, in the respective cases of residual strain of 0.5%, residual strain of 0.8% and residual strain of 1.5%, as shown respectively by FIG. 8, FIG. 9 and FIG. 10, the spatial difference amounts in accordance with the respective domains on the central line L of the test bodies 10 are set and the distribution width which is the difference between the minimum value and the maximum value of the spatial differential amount is gradually reduced as indicated by p2, p3 and p4.

It seems that the distribution widths of the spatial difference amounts of p2, p3 and p4 are reduced in accordance with an increase in the amount of residual strain since an amount of dislocations is increased, magnetically disordered portions are increased and magnetic fields are canceled by each other in accordance with the increase in the amount of residual strain.

From the respective diagrams mentioned above, although a change in the spatial difference amounts is comparatively small in the initial state and the elastically deformed region with 0.1% deformation (after applying elastic force), in respect of the plastically deformed test bodies 10, the spatial difference amounts having considerable variation are respectively obtained. Therefore, the test bodies 10 which have been applied with loads under the elastic limit as shown by FIGS. 5 and 6, can be discriminated from the test bodies 10 which have been applied with loads exceeding the elastic limit as shown by FIG. 7 through FIG. 10 easily by sizes of the distribution widths of the spatial difference amounts.

Such spatial difference amount distribution diagrams on the central line L of the test body 10 shown by each of FIG. 5 through FIG. 10 is formed not only for the central line L of the narrow width portion 10*b* of the test body 10 but in respect of, for example, a line L1 of L+10 mm and a line L2 of L−10 mm both of which are shifted from the central line L in a direction orthogonal thereto as shown by FIG. 4 by sampling similarly the spatial difference amounts with regard to respective domains on the line L1 and L2, respectively (illustration is omitted).

The spatial difference amount distribution diagrams (in correspondence with FIG. 7 through FIG. 10) on the three lines L, L1 and L2 provided in this way are respectively formed for each of residual strains of 0.2%, 0.5%, 0.8% and 1.5% produced by applying loads exceeding the elastic limit. Further, when the distribution widths p1, p2, p3 and p4 of the respective spatial difference amount distribution diagrams are plotted for each of the lines L, L1 and L2 under a relationship of the respective residual strains of 0.2%, 0.5%, 0.8% and 1.5%, the correlation shown by FIG. 11 is obtained.

In FIG. 11, a mark ○ designates the distribution width of the spatial difference amounts of domains on the central line L, a mark □ designates the distribution width of the spatial difference amounts of domains on the line L1 and a mark △ designates the distribution width of the spatial difference amounts of domains on the line L2, respectively.

Further, when the relationship between the amount of residual strain and the distribution width R is recurred by an exponential function with the amount of residual strain designated as $\epsilon$ and the distribution width of the spatial difference amount designated as R based on the diagram showing three kinds of the correlations between the residual strain and the distribution width as follows.

$$\epsilon = 8.9 \times e^{-67R} \text{ (where } e \approx 2.71828\text{)} \qquad (1)$$

Accordingly, in measuring presence or absence of plastic deformation of steel material in, for example, existing structures or the like, the spatial quadratic differential of a magnetic field is measured by scanning the magnetic flux meter 13 nondestructively along surface of the steel material which is a measured body and an equi-magnetism line diagram of the spatial quadratic differential is drawn by which a portion of the equi-magnetism lines having dense intervals can be identified as a plastically deformed portion.

Further, the surface of the steel material which has been subjected to the magnetism measurement is partitioned in predetermined sizes and a difference between a maximum value and a minimum value of a value of the spatial quadratic differential of the magnetic field obtained by the magnetic flux meter 13 is set as the spatial difference amount for each of domains. Further, by sampling the spatial difference amounts at respective domains on lines along a direction of extending the steel material, the distribution width R of the spatial difference amounts is obtained and substituted for Equation (1) by which the magnitude of the residual strain can quantitatively be obtained. The degree of plasticity can macroscopically evaluated by the residual strain.

As described above, according to the embodiment, not only presence or absence and location of plastic deformation of steel material can be identified but a degree of plasticity can quantitatively be evaluated from the distribution widths of the spatial difference amounts.

Further, although according to the above-described embodiment, the spatial quadratic differential of a magnetic field is measured by the magnetic flux meter 13, in place thereof, the magnetic field per se or spatial first order differential of the magnetic field may be measured.

Further, although according to the above-described embodiment, the magnetic field in a direction vertical to the surface of the test body 10 is measured by the magnetic flux meter 13, a magnetic field in a direction in parallel with the surface of the test body 10 may be measured. Likewise, instead of measuring an intensity of a directional component of a magnetic field, an intensity of a synthesized magnetic field may be measured.

Further, the lines L, L1 and L2 for setting the correlations between the spatial difference amounts and the residual strain as shown by FIG. 11 may not be the central line L nor the lines L1 and L2 in parallel with the central line L remote therefrom by 10 mm and domains along other pertinent lines may be used. Further, a number of lines for selecting domains needs not to be three but can be set to a pertinent number which is equal to or more than one.

As has been explained, according to a nondestructive method of quantitatively evaluating a degree of plasticity of steel material of the present invention, the presence or absence and location of plastic deformation of steel material can be identified and, further, an amount of residual strain can quantitatively be evaluated as a degree of plasticity.

What is claimed is:

1. A nondestructive method of quantitatively evaluating a degree of plasticity of ferromagnetic materials, comprising the steps of: measuring a magnetic field of a surface of a ferromagnetic test body using a magnetic sensor; partitioning the surface of the ferromagnetic test body into regions corresponding to domains of the ferromagnetic test body; calculating a difference between a maximum value and a minimum value of a magnetic signal corresponding to the magnetic field for each of the domains as a spatial difference amount; measuring a distribution width of the spatial difference amounts and an amount of residual strain corresponding to an amount of plastic deformation of the ferromagnetic test body; calculating a correlation between the distribution width of the spatial difference amounts and the amount of residual strain; and calculating a degree of plasticity of the ferromagnetic test body in accordance with the correlation.

2. A nondestructive method of quantitatively evaluating a degree of plasticity of ferromagnetic materials according to claim 1; wherein the ferromagnetic test body comprises a steel test body.

3. A nondestructive method of quantitatively evaluating a degree of plasticity of ferromagnetic materials, comprising the steps of: applying a load on a ferromagnetic test body; removing the load applied on the ferromagnetic test body; measuring a magnetic field in each of a plurality of domains of the ferromagnetic test body caused by magnetic anisotropy generated by plastic deformation of the ferromagnetic test body due to the applied load; calculating a difference between a maximum value and a minimum value of the magnetic field in each of the domains as a spatial difference amount; measuring a distribution width of the spatial difference amounts and an amount of residual strain corresponding to an amount of plastic deformation of the ferromagnetic test body; calculating a correlation between the distribution width and the amount of residual strain; and calculating the degree of plasticity of the ferromagnetic test body in accordance with the correlation.

4. A nondestructive method of quantitatively evaluating a degree of plasticity of ferromagnetic materials according to claim 3; wherein the ferromagnetic test body comprises a steel test body.

5. A nondestructive method of quantitatively evaluating a degree of plasticity of ferromagnetic materials according to claim 3; wherein the step of measuring the magnetic field of the ferromagnetic test body comprises scanning a surface of the ferromagnetic test body using a magnetic sensor.

6. A nondestructive method of quantitatively evaluating a degree of plasticity of ferromagnetic materials according to claim 5; wherein the magnetic sensor comprises a magnetic flux meter.

7. A nondestructive method of quantitatively evaluating a degree of plasticity of ferromagnetic materials, comprising the steps of: applying a load on a ferromagnetic test body; removing the load applied on the ferromagnetic test body; scanning a surface of the ferromagnetic test body using a magnetic sensor to measure a magnetic field in each of a plurality of domains of the ferromagnetic test body; calculating a difference between a maximum value and a minimum value of the magnetic field in each of the domains of the ferromagnetic test body as a spatial difference amount; measuring a distribution width of the spatial difference amounts and an amount of residual strain corresponding to an amount of plastic deformation of the ferromagnetic test body; calculating a correlation between the distribution width and the amount of residual strain; and calculating the degree of plasticity of the ferromagnetic test body in accordance with the correlation.

8. A nondestructive method of quantitatively evaluating a degree of plasticity of ferromagnetic materials according to claim 7; wherein the ferromagnetic test body comprises a steel test body.

9. A nondestructive method of quantitatively evaluating a degree of plasticity of ferromagnetic materials according to claim 7; wherein the magnetic sensor comprises a magnetic flux meter.

* * * * *